United States Patent [19]
Bird et al.

[11] Patent Number: 5,216,485
[45] Date of Patent: Jun. 1, 1993

[54] ADVANCED VIA INSPECTION TOOL (AVIT)

[75] Inventors: Kenneth A. Bird, New Paltz; Douglas Y. Kim, Poughkeepsie; Stephen J. Kish, Hyde Park; Julius J. Lambright; Kurt R. Muller, both of Hopewell Junction; Lawrence D. Thorp, Yorktown Heights, all of N.Y.

[73] Assignee: International Business Machines Corporation, Armonk, N.Y.

[21] Appl. No.: 754,794

[22] Filed: Sep. 4, 1991

[51] Int. Cl.$^5$ .............................................. G01N 21/88
[52] U.S. Cl. ...................... 356/394; 356/237; 382/8
[58] Field of Search ............... 356/394, 237; 382/8

[56] References Cited

U.S. PATENT DOCUMENTS

| | | | |
|---|---|---|---|
| 3,636,362 | 1/1972 | Beeman et al. | 250/219 FR |
| 3,750,189 | 7/1973 | Fleischer | 346/74 ES |
| 3,806,252 | 4/1974 | Harris et al. | 356/156 |
| 4,162,126 | 7/1979 | Nakagawa et al. | 356/237 |
| 4,421,410 | 12/1983 | Karasaki | 356/378 |
| 4,681,442 | 7/1987 | Wagner | 356/237 |
| 4,737,650 | 4/1988 | West | 250/571 |
| 4,738,533 | 4/1988 | Iwamoto | 356/237 |
| 5,015,097 | 5/1991 | Nomoto et al. | 356/237 |

FOREIGN PATENT DOCUMENTS

| | | |
|---|---|---|
| 1441386 | 6/1976 | United Kingdom. |
| 2117897 | 10/1983 | United Kingdom. |

OTHER PUBLICATIONS

T. Ninomiya, et al., "Automatic 2½D Shape Inspection System for Via-Hole Fillings of Green Sheets by Shadow Image Analysis" IEEE pp. 515-520, 1989.

IBM Docket No. FI9-91-123 U.S. PTO Application Ser. No. 07/754,830 filed Sep. 4, 1991 entitled "Printing Apparatus".

IBM Docket No. FI9-91-160 U.S. PTO Application Ser. No. 07/754,793 filed Sep. 4, 1992 entitled "Method and Apparatus for Object Inspection".

*Primary Examiner*—F. L. Evans
*Attorney, Agent, or Firm*—Donald M. Boles; Harold Huberfeld

[57] ABSTRACT

A method and apparatus for the inspection and handling of surface level defects is taught. Briefly stated, the object to be inspected is positioned. A Laser light is polarized into at least one orientation and then reflected off of a rotated polygon mirror. This causes the light to "move" over the area of interest. A plurality of fiber optic bundles are used to receive and conduct the reflected light back to photomultipliers. The photomultipliers convert the light into electrical signals while associated electronics digitize the signals, keeping track of pixels which are produced. By keeping track of pixel edge boundaries and determining if certain thresholds are exceeded or not met as appropriate, the area of interest can be checked for a variety of defects. By comparison of the defects to a reference base, the defects and hence the items inspected can be categorized.

5 Claims, 9 Drawing Sheets

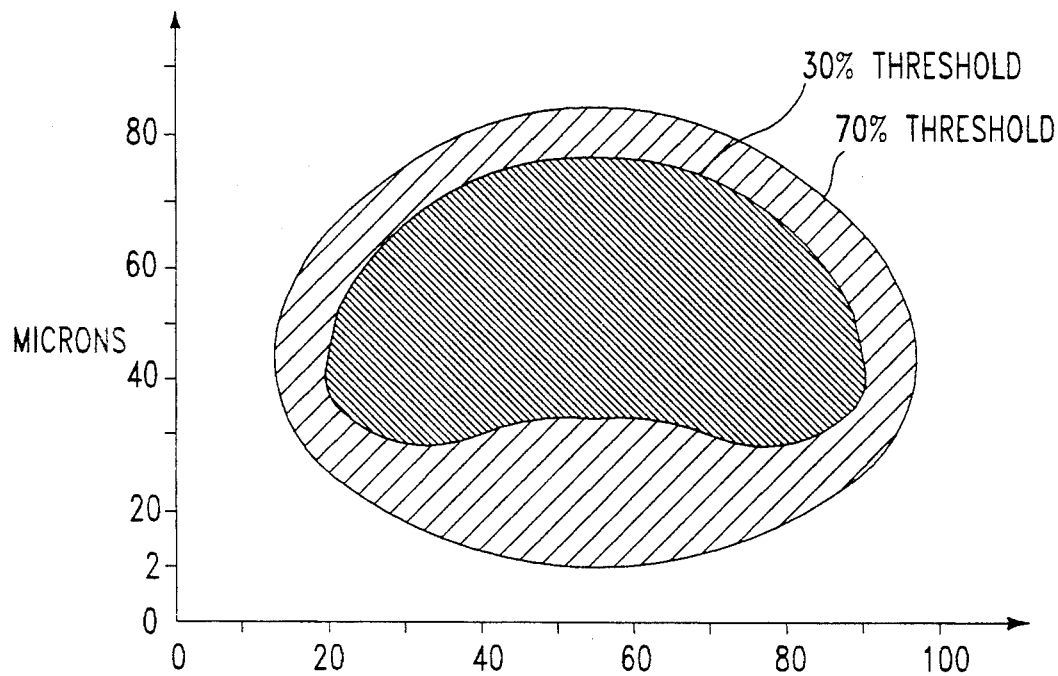
FIG. 5 SPOT POSITION IN THE SCAN DIRECTION
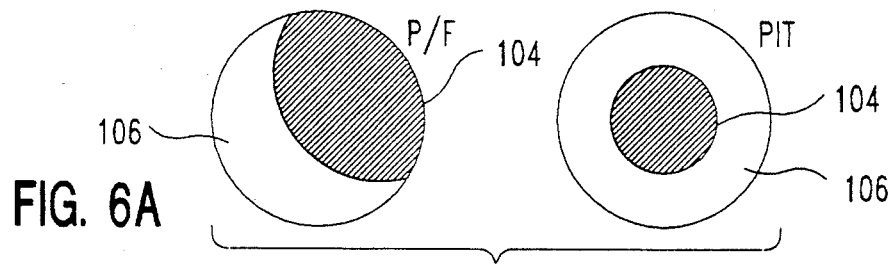
FIG. 6A
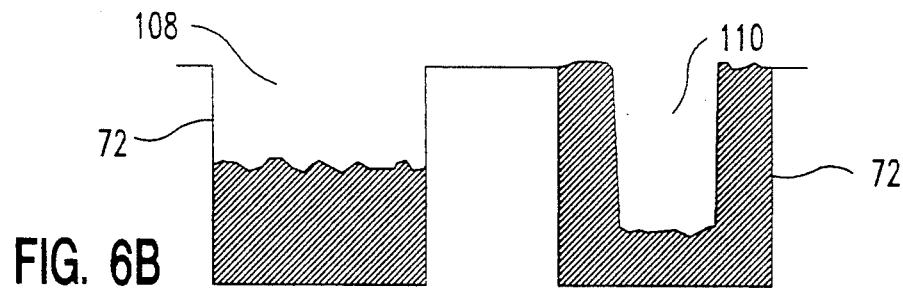
FIG. 6B
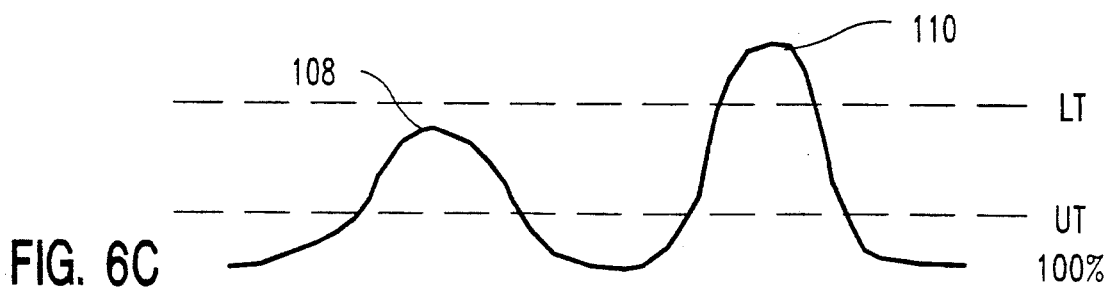
FIG. 6C

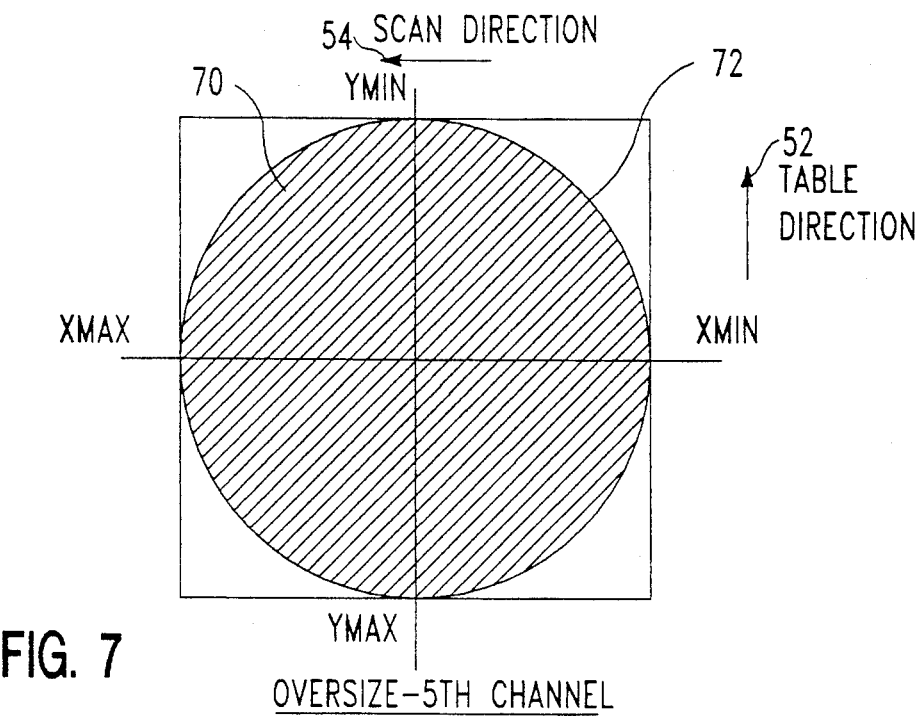
FIG. 7  OVERSIZE-5TH CHANNEL
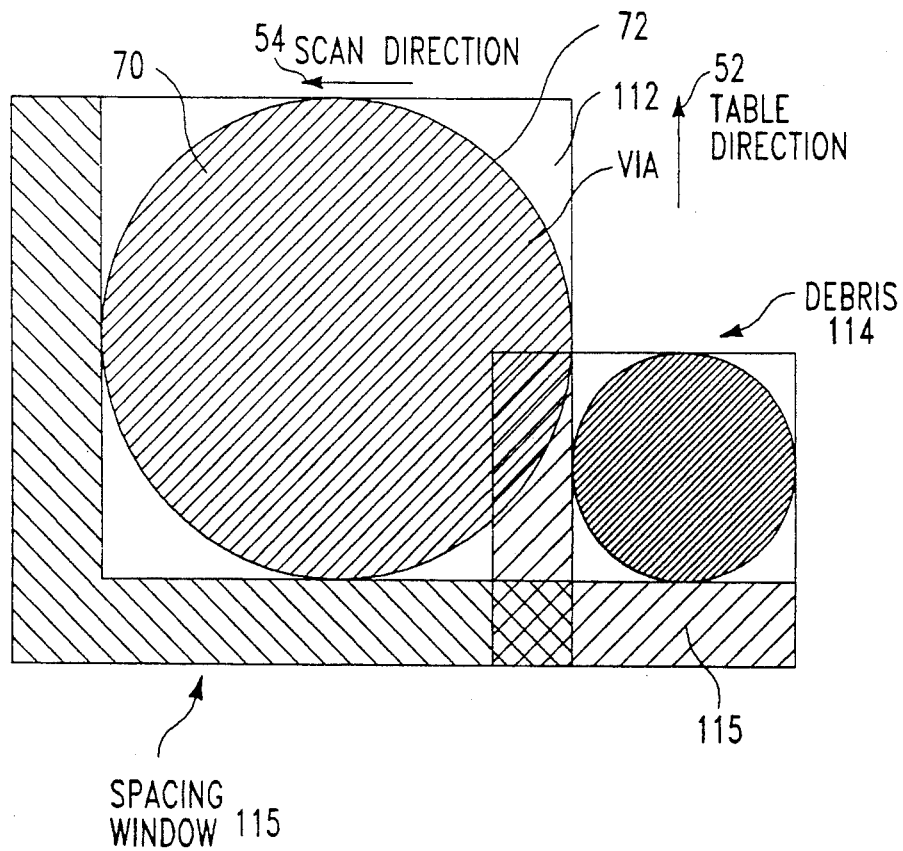
FIG. 8  SPACING-5TH WINDOW

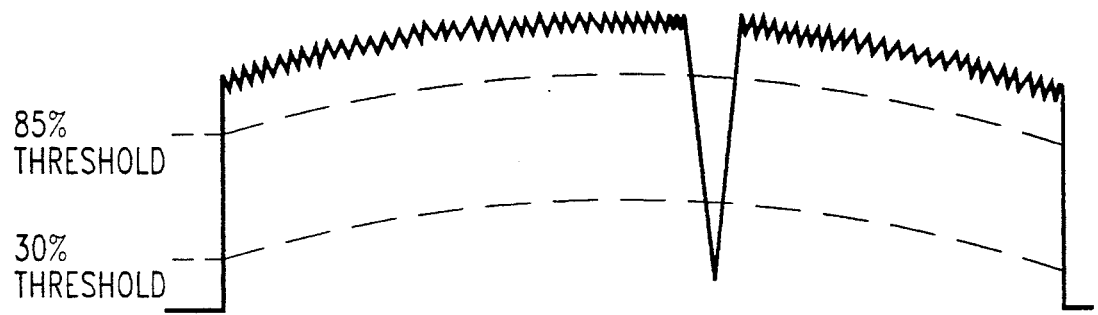
FIG.9A VIDEO WITH SINGLE DEFECT 116
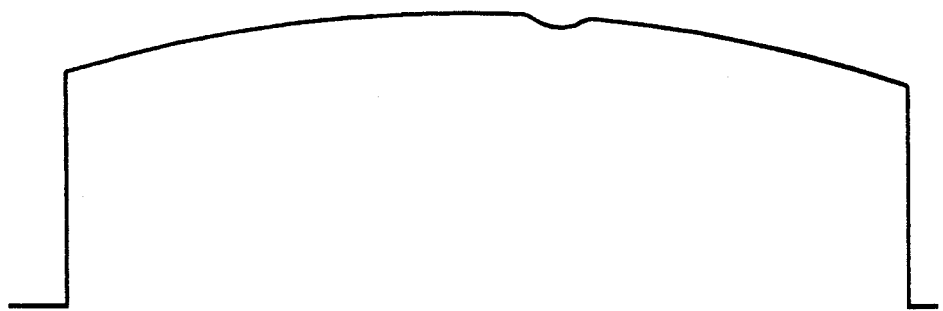
FIG.9B REFERENCE SIGNAL 118
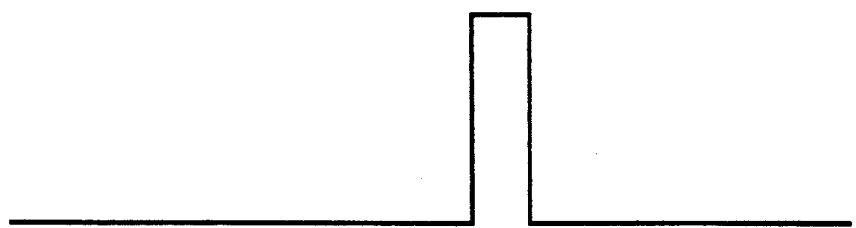
FIG.9C DIGITAL OUTPUT 120

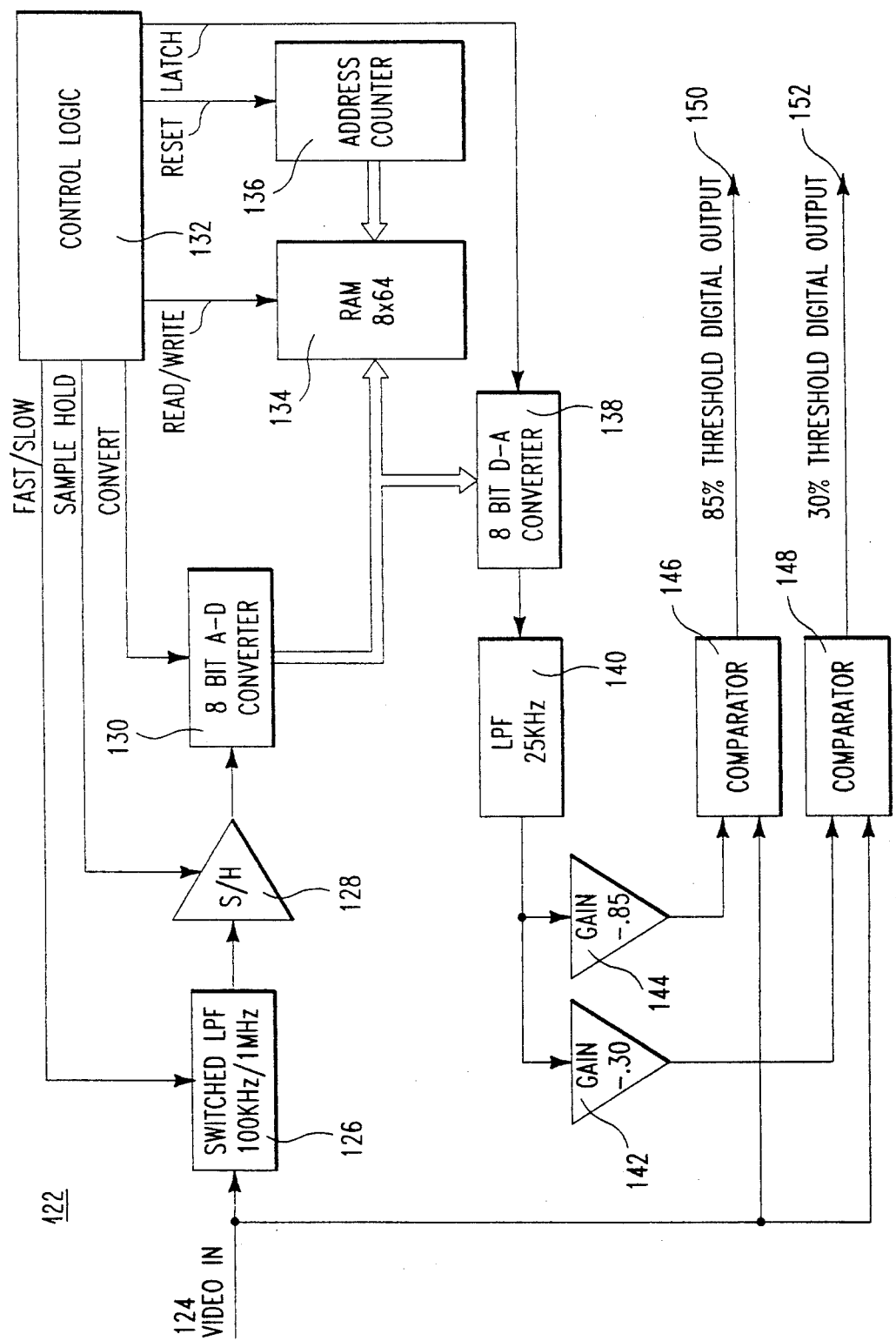
FIG. 12 ANALOGUE PRECESSING ELECTRONICS

ADVANCED VIA INSPECTION TOOL (AVIT)

RELATED APPLICATIONS

This application is related to a co-pending, contemporaneously filed patent application Ser. No. 07/754,830, filed Sept. 4, 1991 and now U.S. Pat. No. 5,135,317 entitled PRINTING APPARATUS, assigned to the same assignee as the present invention and to, co-pending patent application Ser. No. 07/754,793, filed Sept. 4, 1991 and entitled METHOD AND APPARATUS FOR OBJECT INSPECTION, assigned to the same assignee as the present invention.

BACKGROUND OF THE INVENTION

1. Field of the Invention

This invention relates, generally, to a method and apparatus for article inspection and more particularly to an optical scheme for high speed inspection of densely packed areas of interest, utilizing a plurality of optical fibers, a light source and a rotating mirror.

2. Related Art

The manufacture of semiconductor apparatus increasingly moves to more and more dense packaging. Accordingly, this means that although more devices are associated with any component or assembly and hence the total number of packages/devices decreases, the value of each package/device increases.

Further, due to this increased density, it is more and more difficult the produce quality products. One of the contributing factors is that only a small number of defects, any one of which may occur in a variety of steps and processes, may cause the entire end product or component to be defective. Therefore, in effect, due to this increasing density, a smaller number of defects per step, when cumulatively taken in total over a, now more dense product, may result in the production of scrap.

It is therefore more and more important not only to perform each step/process correctly, but it is even more important to inspect each step/process or series thereof for such defects.

This has the effect of placing an increasing burden on the whole process. As these devices and the like become more dense, the complexity of testing increases.

This problem is particularly evident in the production and testing of multilayer ceramics (MLC). A MLC performs essentially like a multitude of layered circuit boards. Each layer, in the art referred to as "green sheets" has a plurality of apertures or "vias" therein. During manufacture, these vias must be filled with an electrically conductive paste. Thereafter, these filled vias are overlayed onto an adjacent green sheet, also containing vias. In this fashion a "sandwich" is formed having conductive circuit paths therethrough and therein so as to form an extremely dense MLC "brick".

By way of illustration, a typical layer in a glass ceramic product may have 50,000-200,000 (and theoretically more) vias, over an active area of 160 mm × 160 mm (slightly more than 6 inches square). Due to such densities, and driven by the need to inspect each via, visual inspection is extremely difficult. Such inspections should ideally consider or check for full or partially filled vias, overfilled vias, registration of the vias and the like.

Unfortunately, it has heretofore been not only difficult to check for such parameters, but the time to do so has been prohibitively long. Some devices, readily available on the market may take minutes to accomplish such testing, with only a moderate degree of reliability. Should it become necessary to inspect more than a few number of green sheets in any given day, the time required for testing simply would not allow for testing of an entire daily production run.

Therefore, the choice is for the usage of untested product, or the hold-up of production until testing can be done. However, in the economic manufacturing environment as is present today, either choice is not a competitive solution.

A number of schemes have been disclosed which have been attempted. Such methods include an article by Ninomiya, et. al. entitled "Automatic $2\frac{1}{2}$D Shape Inspection System for Via-Hole Fillings of Green Sheets By Shadow Image Analysis, IEEE, 1989, Ch2750-8/89, pps 515-520. There, a system is disclosed which uses shadow imaging theory for via inspection. However, this scheme is not practical for large scale, dense green sheets in that the front-end optics are simply inadequate for precise, fast testing. In a sample 160 × 160 mm greensheet, it has been judged that the Ninomiya method would require over $2\frac{1}{2}$ minutes for testing, produce approximately, 0.6 false alarms per sheet, would require an extremely high power light source, and would operate at a very low pixel rate.

A second solution was suggested in U.S. Pat. No. 4,737,650, entitled "Inspection Apparatus" and issued Apr. 12, 1988 to West. While this reference describes a scanning apparatus, it does not address the means to handle large amounts of pixel data which this would create.

U.S. Pat. No. 4,421,410, entitled "Method and Apparatus for Inspecting Printed Wiring Boards" and issued Dec. 29, 1983 to Karasaki is limited in the size/number of defects which are detectable.

U.S. Pat. No. 4,162,126, entitled "Surface Detect Test Apparatus", issued Jul. 24, 1979 to Nakagawa, et. al. is for testing only particular types of surface defects and by virtue of its scheme, is simply too slow for high density green sheets.

British Patent 1,441,386, entitled "Scanning Apparatus", Published Jun. 30, 1976 discloses merely an optical scheme for a moving/oscillating mirror and as such is incomplete and inherently slow.

A publication entitled "Three Laser Scanning Instruments for Automatic Surface Inspection" for British Steel Corporation, pps 102-110, by R. N. West similarly lacks a scheme for handling large amounts of data collected.

U.S. Pat. No. 3,750,189, entitled "Light Scanning and Printing System" issued Jul. 31, 1973 to Fleischer discloses an optical system essentially for use in present day facsimile machines and hence lacks the accuracy required.

U.S Pat. No. 4,681,441, entitled "Method for Surface Testing", issued Jul. 21, 1987 to Wagner discloses a fiber optic collection scheme which is deficient in that it lacks the speed required for fast optical scanning given the required resolution.

U.S. Pat. No. 4,738,533, entitled "Plywood Surface Defect Detecting Head", issued Apr. 19, 1988 to Iwamoto discloses a course system of optical inspection.

U.S. Pat. Nos. 3,806,252 entitled "Hole Measurer", issued Apr. 23, 1974 to Harris, et. al. and 3,636,363, entitled "Device for Measuring Hole Sizes", issued Jan. 18, 1972 to Beeman, et. al. describe only mechanisms which are not fast AND are not sufficiently accurate for measuring small aperture diameters.

U.K. Patent Application 2,117,897, entitled "Detecting Surface Defects", filed Apr. 3, 1983 effectively provides only a "1" dimensional look of a surface and hence is simply not suitable for Green Sheets.

OBJECTS AND SUMMARY OF THE INVENTION

Accordingly it is an object of the present invention to produce a device which can inspect vias, apertures, surfaces and surrounding areas.

It is another object of the present invention to produce a device which can is readily reconfigurable to inspect a variety of devices.

Yet another object of the present invention is to produce a device which can test for a variety of defects such as re-workable and non-reworkable.

Still another object of the present invention is to produce a device which is automated.

Another object of the present invention is to produce a device can handle large amounts of data in an extremely fast fashion.

A further object of the present invention is to produce a device which uses optical scanning and having low power requirements.

It is a still further object of the present invention to produce a device which has relatively few moving components, thereby reducing the amount of wear and tear.

It is another object of the present invention to produce a device which does non-contact testing of a green sheet.

Another object is to produce a device which is extremely precise and examine and evaluate densely packed areas of interest.

Yet another object of the present invention is to produce a device which can detect and account for or ignore contamination which is adjacent the area of interest.

A further object of the present invention is to produce a via screening inspection system, comprising a means for translating in a first direction a substrate having a plurality of areas of interest, at least one optical energy source, a means for scanning the light source across the substrate, a telecentric f-theta lens positioned between the substrate and the scanning means such that the scanned beam maintains a predetermined angle with respect to the substrate surface as it scans across the surface, a series of optic fibers located at a plurality of angles to the substrate operative to receive reflections of the scanned beam from the substrate, photomultiplier means connected to the optic fibers for converting the reflected light to an electrical signal, and processing means for analyzing the electrical signal, wherein the processing means compare the signal received from a series of scanning lines with reference values to determine acceptability of the area of interest. Such a device is taught by the present invention.

BRIEF DESCRIPTION OF THE DRAWINGS

Reference may now be had to the accompanying drawings in which:

FIG. 5 is a pixel map representation of a partial via fill;

FIG. 6A-6C show the difference between a partial via fill and a pitted via fill;

FIG. 7 shows a representation of an overfilled via fill;

FIG. 8 shows how spacing violations between adjacent vias are viewed;

FIG. 9A-9C show the actual and reference electrical signals for detecting defects;

FIG. 10 is a block diagram of the analog processing electronics of the present invention;

DETAILED DESCRIPTION OF THE PREFERRED EMBODIMENT

SYSTEM OVERVIEW

The present invention is generally comprised of three sub-systems/components; a transport mechanism, an optics inspection scheme and an electronics sub-system, the latter two being described in significant detail below.

Figure 1:
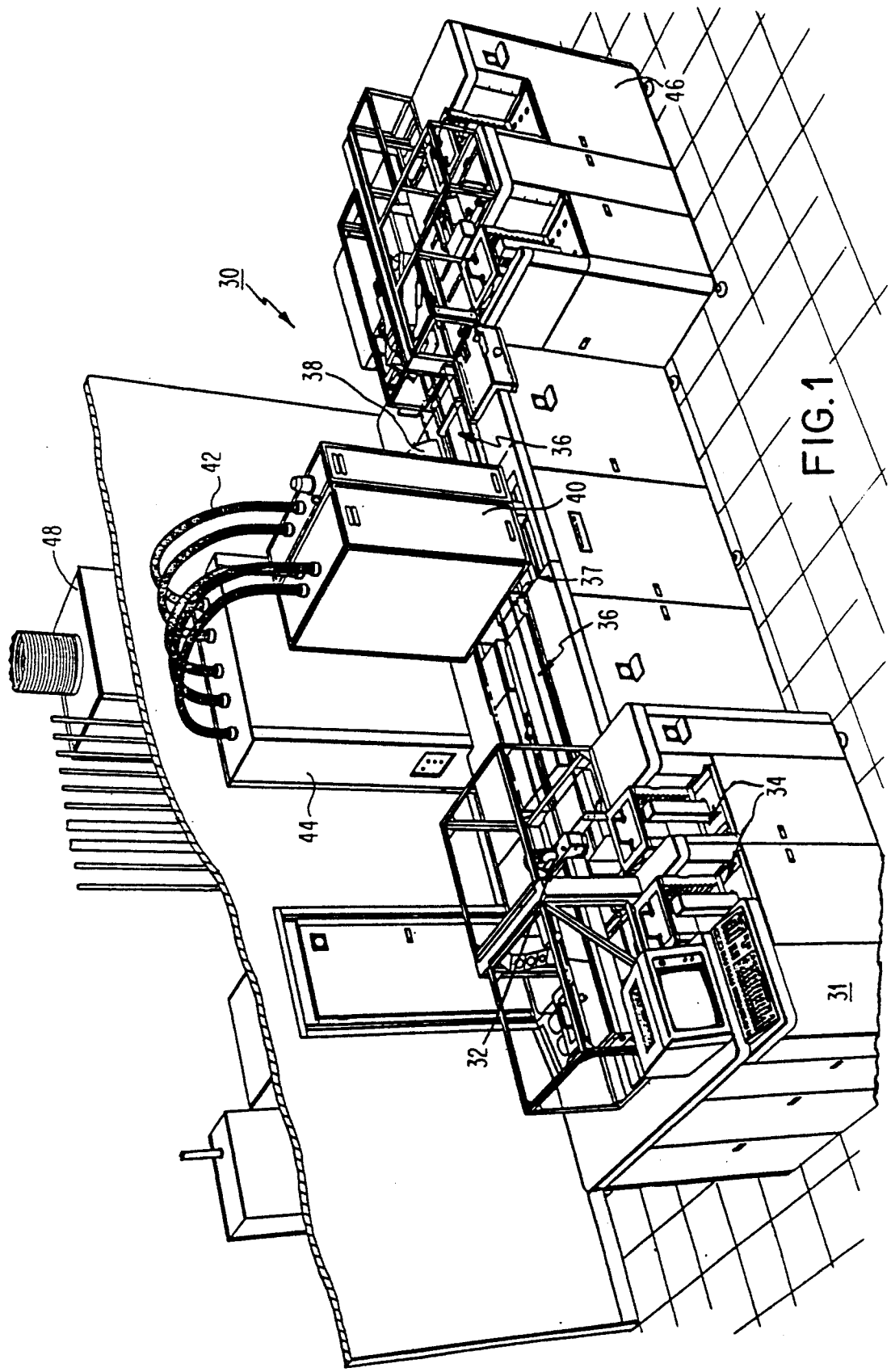
FIG. 1 shows a perspective view of an inspection apparatus in which the apparatus of the present invention may be used.

Referring now to FIG. 1 there is shown a perspective view of the via inspection tool 30 for preferred utilization of the present invention. The via inspection tool 30 is comprised of a input station shown generally at 31. The input station 30 has therein a MLC magazine section 34 for the receipt of green sheets (not shown). Adjacent the MLC magazine section 34 is a cleaning station 32 for cleaning of green sheets.

An air track 36 is utilized for moving the green sheets through the inspection area 37 of the present invention. A sequence printer 38 is utilized for marking the green sheets after inspection, the operation of which is described more fully in the application Ser. No. 07/754,830, now U.S. Pat. No. 5,135,317.

The inspection area 37 is generally comprised of an optics tower 40 having fiber bundles 42 attached therethrough. The fiber bundles 42 are attached at their remaining end to a receiver box 44. An electronics console 48 is operatively connected to the receiver box 44 and the via inspection tool 30.

Inspected greensheets pass through the inspection area 37 to the output station 46 where they are restacked according to their different characteristics, i.e. passed inspection, scrap, reworkable, etc.

Accordingly, the via inspection tool 30 is used to receive, transport/orient the green sheets, check the vias, and sort according to test results, all in 1 continuous operation.

In order to fully understand the operation of the via inspection tool 30, the following overview is offered, with detailed operations described thereafter. During actual operation a number of steps are accomplished. The green sheet is first loaded into the input station 31. It is then registered on a precision transport table. The green sheet is then moved to the inspection area 37 where a laser scan is performed (as described more fully below). A reference signal is obtained from this laser scan of a "clean sheet" area of the green sheet. By "clean sheet" area is meant the via free leading edge of the green sheet. This reference signal sets the threshold level for further inspection, i.e. the three light levels of reflected laser light, black, white and gray.

As the green sheet moves under a scan lens, a complete raster scan of the entire via array region laser light provides a video signal which is sampled at discrete angles by a five channel fiber optic sensor assembly. The five channel fiber optic sensor assembly contains five independent photomultipliers. The feature extraction of each via is performed within a high speed electronic processor assembly which preferably operates at 87 Mhz. The dimensions of the largest feature are determined in the x,y and z coordinate range for each via. As a result a full disposition of each green sheet is made by the processor electronics.

The green sheet is then marked by printing, as previously mentioned and then moved to the output station 46 for disposition.

OPTIC SUB-SYSTEM

In the preferred embodiment, the optical configuration was determined based upon 4 inspection requirements. However, it is to be remembered that other criteria may be used without departing from the spirit and scope of the present invention. These 4 requirements are:

Partial fill detection (Z axis)- the ability to detect the absence of conductive paste in the via deeper than a predetermined distance from the surface of the green sheet. In the event of sloped or inadequate fill measurement to the shallowest point;

Oversize detection in order to determine if the conductive paste in the via exceeds a predetermined set limit in the X or Y direction;

Spacing detection to determine if any paste is beyond-/violates a predetermined set boundary around each via in order to ensure that there will not be two or more adjacent spacing violations in the via pattern, thereby eliminating a chance of a short; and Contamination detection to determine any contamination within a preset window.

Figure 2:
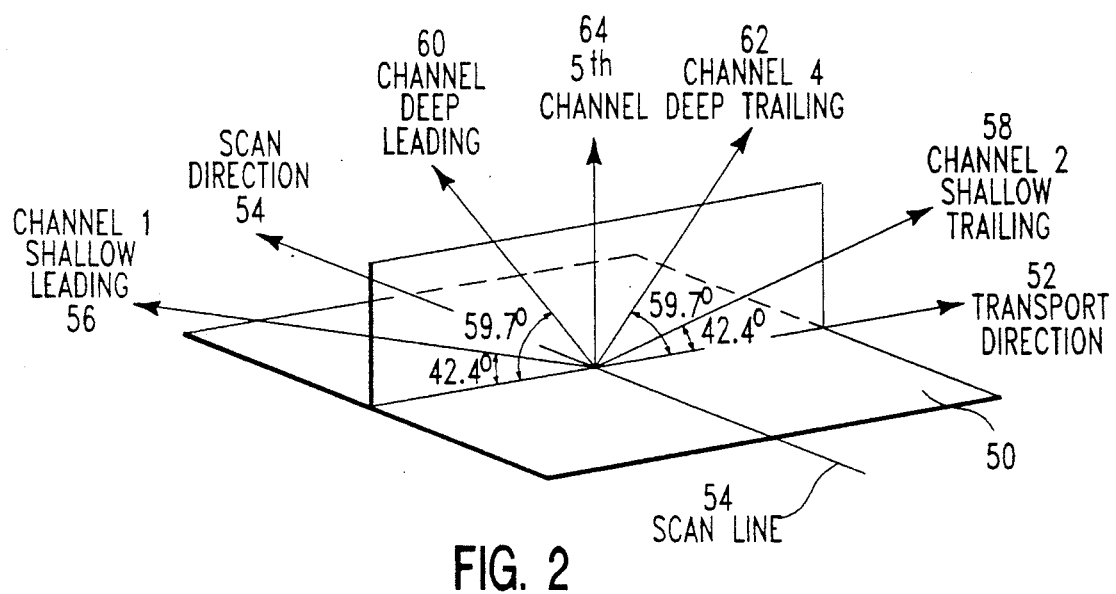
FIG. 2 shows the orientation of the device to be inspected with respect to the optical scanning lines.
Figure 3:
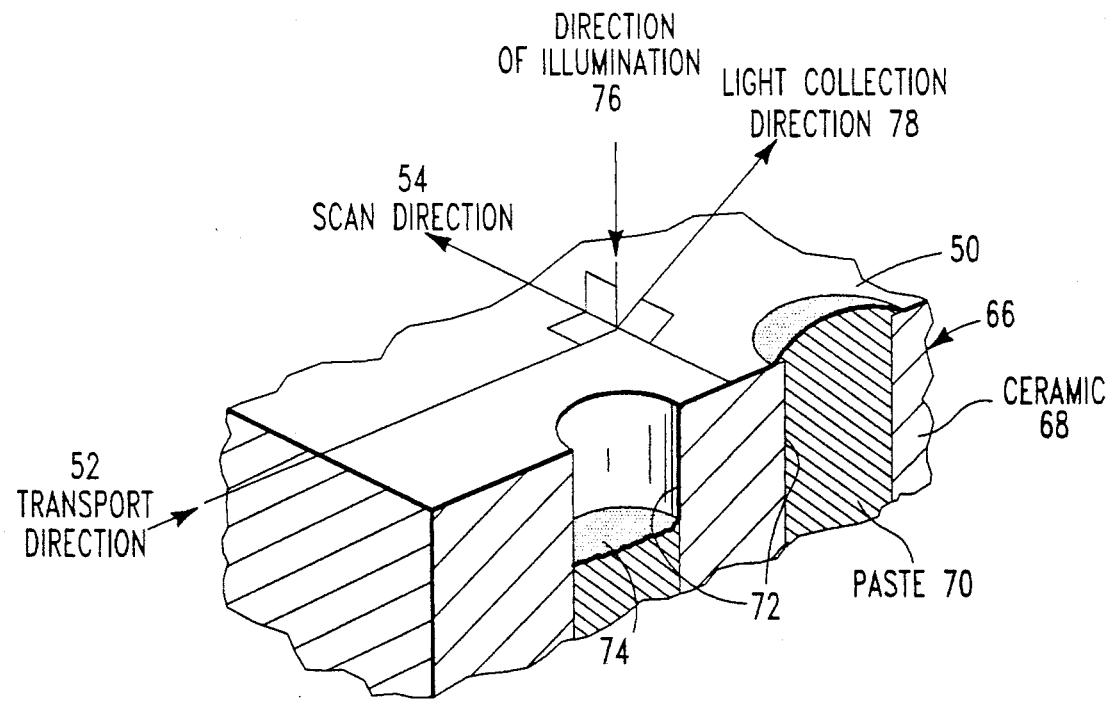
FIG. 3 shows a more detailed view of inspection of a via.

Referring now to FIGS. 2 and 3 there is shown in diagramatic form the scheme for optical laser scanning of green sheets and vias in the preferred embodiment of the present invention. More particularly, shown is a sheet surface 50 which is to be inspected. Each sheet surface is oriented in two directions. A transport direction 52 which is the direction in which the green sheet travels the via inspection tool 30. A scan line direction 54 is perpendicular to the transport direction 54 and is the direction in which the laser scans the sheet surface 50.

In the preferred embodiment of the present invention five optical channels or laser paths are utilized to inspect the green sheet surface 50. Light is shone on the green sheet surface 50 in a direction of illumination 76 which is essentially perpendicular to the green sheet surface 50 and moved along the scan line by use of a rotating mirror or spinner 210 (shown in FIG. 11 and described more fully below). This in essence moves the direction of illumination 76 so as to move over the scan direction 54. Then as the green sheet moves in the transport direction 58, the entire green sheet surface may be "scanned" thereby having the laser illuminate each area and hence each via 72 and each adjacent area. Light is therefore reflected back from the particular area where it is being shone.

A number of optical channels, which in the preferred embodiment of the present invention total five, are positioned so as to receive the reflected light. It is to be understood that the number of channels may be increased or decreased as desired, without departing from the spirit and scope of the present invention. In the preferred embodiment of the present invention the orientation of the channels is as follows, and as depicted in FIG. 2:

1. Channel 1—(item 56)—shallow leading is 42.4 degrees from the plane of the sheet surface 50;
2. Channel 2—(item 58)—shallow trailing is also 42.4 degrees from the plane of sheet surface 50, but measured from the opposite side of the scan line;
3. Channel 3—(item 60)—deep leading is 59.7 degrees from the plane of the sheet surface 50, that is the same direction as Channel 1;
4. Channel 4—(item 62)-deep trailing is also 59.7 degrees from the plane of sheet surface 50, but is measured in the same fashion as Channel 2, from the opposite side of the scan line of Channel 1; and
5. Channel 5—(item 64)—normal to sheet surface (in the "Z" direction from the sheet surface 50).

It has been found that the above 5 channels, in the orientation mentioned provide sufficient resolution for the vias 72 of the present invention, although different areas of interest to be inspected may have different numbers and orientations of the channels.

In the preferred embodiment of the present invention, Channels 1-4 (58-62 inclusive) are each comprised of bundles of two hundred one millimeter optical fibers aligned in two, one hundred strand rows for light collection. The fifth channel 64 uses a single fiber for the retro-reflected signal as previously mentioned. These fibers comprise the fiber bundles 42, terminating in the receiver box 44. The thresholding for these signals are set so that the surface of the green sheet 68 forms the base of 100% level, while the paste levels are set for 70% in the fifth channel 64 and 30% for the obscuration level in the remaining 4 channels, 58-62 inclusive.

In the preferred embodiment of the present invention the optical system of the present invention uses a laser scanner to illuminate normal to the green sheet 66 with an 18 micron HeNe spot. The reflected light is picked up on 5 separate channels for processing. Channels 1 and 2 determine the Channels 3 and 4 calibrate the obscuration area for the vias 72. Channel 5 is for retro-reflection and looks for the contrast between the conductive paste 70 and the green sheet 68 in order to determine spacing, oversize, contamination, and if the via 72 has a depression 74 in the center (generally classified as a pit), which is classified as a partial fill defect so as to minimize false errors by the erroneous indication or classification as an unfilled via.

Figure 4A:
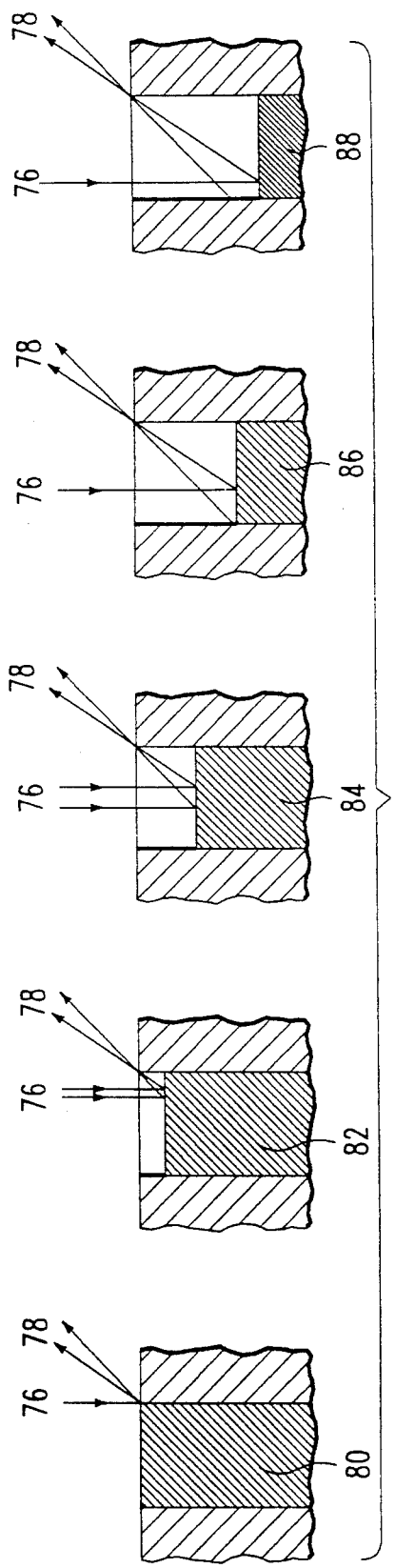
FIG. 4A and 4B show how partial via fill is detectable.
Figure 4B:
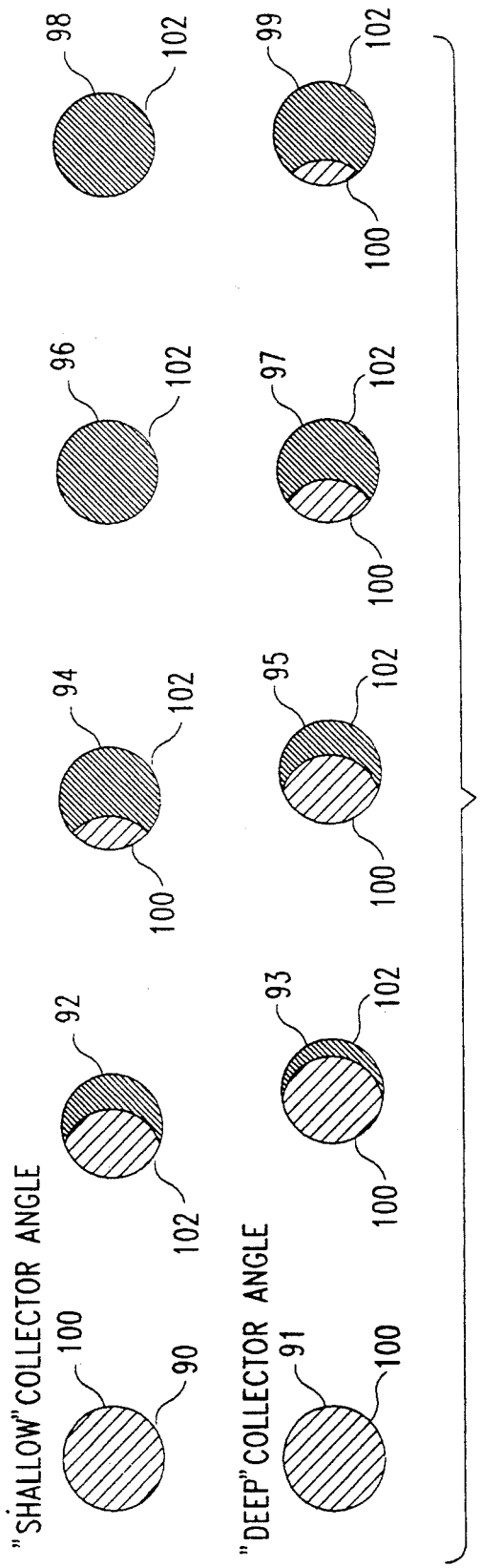

Referring now to FIG. 4, there is shown a series of representations of various amounts of via fill amounts, ranging from the fullest via 80 to the least filled via 88. Shown is the direction of illumination 76 and the various angles of reflected light 78. Here it can be seen how the angle at which the light reflected is dependent upon the position along the scan direction. Also evident is how the amount of light reflected is dependant upon the amount of via fill. By way of example, if the direction of illumination 76 as shown in the fullest via 80 were in the same position, but only a partially filled via 82-88 were being observed, the amount of and angle of reflected light 78 would change dramatically from zero to full intensity and be received by Channels 1-5 (items 56-64 inclusive).

Accordingly, referring to the "Shallow" and "Deep" collector angles as shown in FIG. 4, it can be seen that:
1. in the event of a fully filled via 80, the shallow and deep collector angles 90,91 respectively, from channels 1-4 receive the same amount of conductive paste reflected light 100;
2. in the event of a partially filled via 82, the shallow and deep collector angles 92,93 respectively of channels 1-4, although receiving essentially the same amount of shadow 100, each receive a partial or diminished via fill reflection 102 which is less illumination than the fully filled via 80;
3. in the event of a less partially filled via 84, the shallow and deep collector angles 94,95 respectively of channels 1-4, receive differing amounts of shadow 100, and each receive a partial or diminished via fill reflection 102 which is less illumination than the vias 80, 82;
4. in the event of an even less partially filled via 86, the shallow and deep collector angles 96,97 respectively of channels 1-4, receive none and a 100, and each receive respectively no and partial via fill reflection 102 which is less illumination than the vias 80, 82, 84; and
5. in the event of a minimally filled via 88, the shallow and deep collector angles 98,99 respectively of channels 1-4, receive no reflected light 100, and each receive respectively no and partial via fill reflection 102 which is less illumination than the vias 80, 82, 84, 86.

Accordingly, in the above fashion comparisons can be easily made to a reference via or set of vias as well as to adjacent vias. This in effect can determine the "amount of goodness" of the vias which can be changed on a dynamic basis without redesign and the like.

Referring now to FIG. 5 there is shown a pixel map representation of a partially filled via in graphic form showing the spot position in the scan direction versus the green sheet position in the transport direction. This pixel map is made by the interaction of the receiver box 44 and the electronics console 48 as described more fully below. A partial fill determination can be made by comparing the number of pixels for a given feature that exceed the 30% threshold with that of it's opposing channel (i.e. channels 1 with 2 and 3 with 4). In the preferred embodiment of the present invention, the lowest of the two area values are used to determine if a predetermined value is surpassed corresponding to the depth to be detected. This predetermined value, in the preferred embodiment of the present invention is software set, although firmware or simple flagging could be utilized without departing from the spirit and scope of the present invention.

Referring now to figure six, there is shown how the fifth channel 64 is used to differentiate between a partially filled via 108 and a pitted via 110. In order to prevent a pitted via from being flagged as a partially filled via, an algorithm is preferably used. Channels one and two 56,58 are set so as to have lower and upper limits. As long as the obscuration area does not exceed the lower limit then, by definition it is considered a good via. If the level of obscuration is greater than the lower limit, but less than the upper limit, it is considered a deep partial fill which is not repairable. If the obscuration exceeds the upper limit, the fifth channel 64 threshold is used. If it does not exceeds this fifth channel threshold, it is considered a repairable partially filled via. If it does exceed this fifth channel threshold, it is considered to be a pit of acceptable dimensions and passed on as a good via.

This detection scheme, could in some circumstance be considered acceptable, even though the deep channel 3,4 (items 60,62) are not used. However, in the preferred embodiment of the present invention, the deep channels are used to provide greater flexibility and to more accurately judge the "quality" of the via fill. Accordingly, the deep channels are used/compared in much the same fashion as the shallow channels 1,2 (items 56,58) recited above. Additionally, comparisons may be made between the different sets of channels, i.e. deep to shallow, etc.

Referring now to FIG. 5, a diagramatic view of how oversize detection is handled is shown. This oversize detection is accomplished by the use of the fifth channel, 64. Shown is a plot of the conductive paste 70 in relation to the via 72, in an X-Y graph format, using the scan direction 54 as the X-axis and the periphery of the via 72 is shown the boundary area 112. In practice, the present invention considers or looks for the rising and falling transitions of each feature in order to determine the upper limit in the X and Y axis directions. A "box" or boundary area 112 is then algorimithicaly constructed and in effect if the X or Y values exceed a predetermined limit in either axis, the via 72 is flagged as being oversized. In this fashion, via size and hence oversize conditions may be changed without a change in the hardware/optical system of the present invention.

Accordingly, it is readily evident how the fifth channel 64 may also be used for spacing detection/violations. Referring now to FIG. 8, there is shown a diagramatic plot, similar to FIG. 7 showing how spacing is considered. Again, the boundary area 112 is considered. However, processing further than oversize detection is performed. In the preferred embodiment of the present invention, a zone is effectively constructed from the trailing edge of the feature in the X and Y axis. This zone is done for all features including contamination or debris 114. In the event that anything is written into the spacing windows, a spacing violation is declared, which can be handled as desired, i.e. scrap, etc. Further, in the preferred embodiment of the present invention, the corners of the spacing windows 115 can be algorimithically "rounded" in order to allow for inspection of even tighter geometries.

Contamination or debris 114 is handled by considering their limits in the X and Y axis. If they are below a predetermined limit, the debris 114 is ignored as being too small so as to be detrimental to the product. Accordingly, should this limit be exceeded, the product is flagged, i.e. scrap, re-work, etc.

Figure 11:
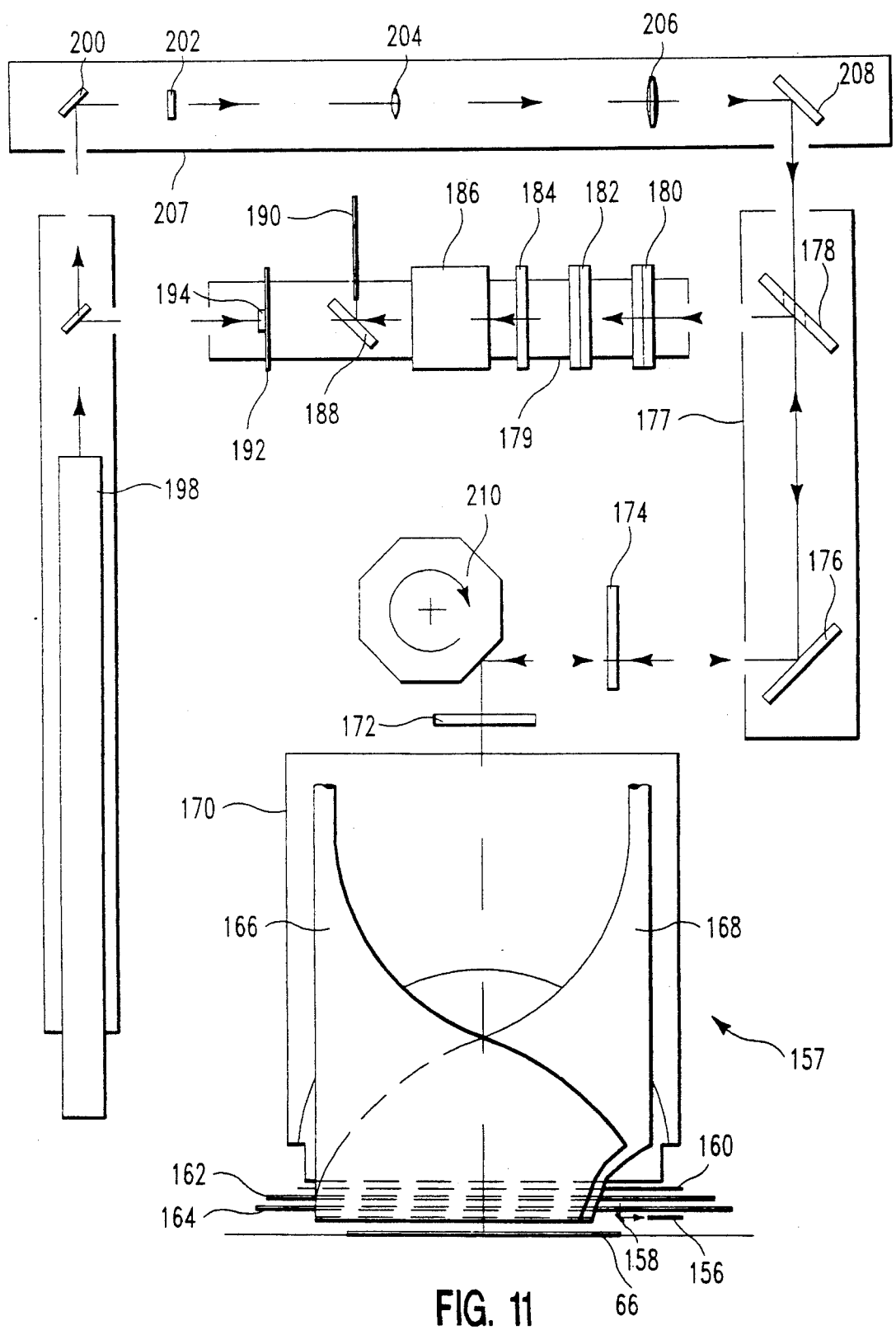
FIG. 11 shows the optical layout of the scanner of the present invention.

The optical scanner of the present invention is a multi-channel system utilizing a rotating polygon mirror system. A good overview of this scheme may be seen by referring to FIGS. 11 and 12, in which FIG. 11 is a diagramatic representation of the optical path of the laser and FIG. 12 is a more detailed diagramatic representation of the lens assembly.

In the preferred embodiment of the present of a laser bench 199 formed from a HeNe laser 198, preferably having a power output of approximately 9 mW. Laser light emanating from the laser 198 first strikes the laser power beam splitter 196 which diverts the laser light to a laser power detector 194 which forms a status monitor 192, thereby enabling the continuous operation of the laser. The laser light also enters the beam shaping bench 201, first striking the 1st beam steering mirror 200. The laser light then passes through the first cylindrical lens 202 and then the 2nd cylindrical lens 204. The light exiting the 2nd cylindrical lens 204 then passes through doublet 206 before striking the 2nd beam steering mirror 208, and thereby exits the beam shaping bench 201. The light then enters the beam steering bench 177, passing through the hole-in-plate beam splitter 178. The laser light emanating the beam splitter 178 then strikes the 3rd beam steering mirror 176.

The light striking the 3rd beam steering mirror 176 from the hole-in-plate beam splitter 178 is passed through the spinner window 174 which then strikes one of the eight surfaces of spinner 210. The light striking a facet of spinner 210 is passed through spinner window 172 which is then directed through scan lens assembly 157 and then onto greensheet 66. Some of the light striking the surface of greensheet 66 using retroreflection is reflected back and thereby in turn passes through spinner window 172, reflects off a facet of spinner 210, through spinner window 174 and reflects at 90 degrees from the surface of the third beam steering mirror 176. This return light, due to its low intensity, only strikes the surface and is reflected 90 degrees from the hole-in-plate beam splitter 178. Upon entering the 5th channel bench 179, the light passes through the convex cylindrical lens 180, the concave cylindrical lens 182 and through the polarizer 184. The light then passes through lens 186 before striking the 5th channel mirror 188 which then enters the 5th channel fiber 190.

The scan lens assembly 157 has a number of fiber bundles, as previously described, contained therein. Shown are two such fiber bundles, one for Channel 1 (item 166) which is used for shallow leading and one for Channel 3 (item 168) which is used for deep leading as referred to in FIG. 2. The scan lens assembly 157 is adjacent the upper and lower cylindrical lenses 162,164 respectively so as to enable the scanning of the surface of green sheet 66. A start of scan mirror 158 is used to provide an initialization or start/stop point for the laser system which is used in conjunction with a start of scan fiber. A stop 160 is provided for registration purposes.

Figures 12A, 12B:
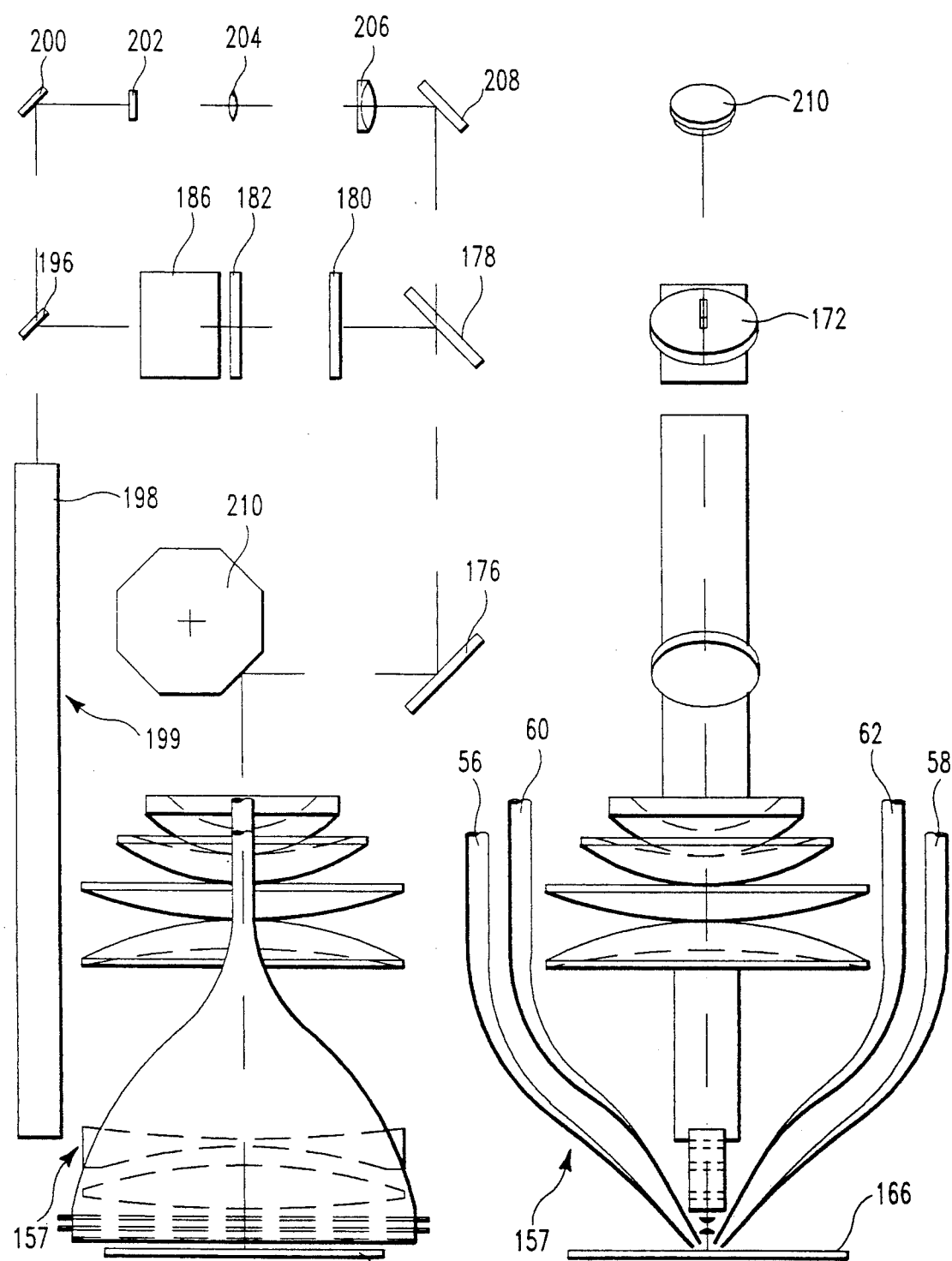
FIGS. 12A and 12B show in more detail the lensing scheme of the scanning lens assembly of the present invention.

Referring now to FIGS. 12A and 12B a more detailed representation of the scan lens assembly 157 can be seen. Shown is the orientation of the channel fibers 56,58,60,62 with respect to the green sheet 66 and the lenses within the scan lens assembly 157.

As previously mentioned, the optical scanner subsystem of the present invention us a multi-channel laser based rotating polygon mirror system. This system, in the preferred embodiment of the present invention uses a flat field telecentric anamorphic f-theta lens system to generate a contiguous raster from a 17 micron size flying spot which is projected onto a moving ceramic green sheet.

The laser source is preferably "s" polarized and is directed to pass through laser power detector 194 which is a 1% power level sensor photodiode. The light also impinges upon the the 1st beam steering mirror 200 which is a maximum reflectance multi-layer dielectric (MLD) fold mirror which directs the beam through the 90 degree rotation shown. The light is then directed into the input aperture of an anamorphic beam shaper-expander which is in effect an anamorphic telescope consisting of two input cylindrical lenses 202,204 oriented orthogonally to each other and an output spherical doublet 206. In the tangential plane, the first cylindrical lens 202 has optical power while the second cylindrical cylinder 204 has none. In this plane the system functions as a "focusing telescope", converging the intermediate image down to a slit width onto a facet of the polygon spinner 210.

It is to be understood that in the preferred embodiment of the present invention, the spinner may have more or fewer facets without departing from the spirit and scope of the present invention. Additionally, more than one laser may be utilized, while the orientation or direction of illumination 76 (FIG. 3) may be at a different angle than perpendicular to the surface which is being inspected.

In the sagittal plane, first cylindrical lens 202 has no optical power and therefore the system 204 having optical power, working against the output spherical doublet 206 which results in a collimated bundle, approximately 10.8 mm in width impinging on the facets of the polygon spinner 210. Accordingly, the shaper-expander 201,177 respectively, has generated a slit of approximately 130 microns in height and 10.8 mm in width which is then incident on a facet of the polygon spinner 210 after passage through the spinner window 172, a MLD coated window. Accordingly, the laser light is now in the correct cross-sectional area for reflected light to pass through the cross-sectional area of the fiber bundles as previously mentioned.

Therefore, the rotating polygon mirror spinner 210 sees an input laser illumination slit which is 10.8 mm wide in the sagittal plane and is 0.130 mm high in the tangential plane. The light is now passed over the full (plus, minus 30 degree) facet rotation, passing through the output window of the spinner housing and entering the anamorphic telecentric f-theta scan lense 157.

The layout of the telecentric anamorphic f-theta scans lens 157 as shown more fully in FIG. 12 is comprised of a number of elements, The first four elements of the lens, measured from the polygon facet, satisfy the f-theta condition meaning that the normal pincushion distortion effect usually apparent when a scanning light bundle crosses the entrance pupil of a spherical lens has been corrected. Rather than ray positions in object space following a tangent (theta) curving of the field in image space, all object coordinates will impinge in image space in a linear manner following a focal length x Theta function. Accordingly, this compensation for "natural" distortion is accomplished by lens element curvature and spacing adjustment along with placing the entrance pupil of the lens at the facet of the polygon spinner 210, or external to the lens. This external entrance pupil distance has been found to be critical and in effect determines the best position of the polygon facet.

Approximately 99 mm from the back surface of element #4, as previously mentioned, is an air-spaced doublet consisting of a negative element coupled with a positive element. This doublet acts as a field flattener and adds a further correction to the telecentricity of the lens system in the sagittal plane. Another, adjacent cylinder lens doublet contributes no optical power to the lens in the sagittal plane. However, the added telecentricity introduced by the field flatteners allows for passage of the scan line cone through the cylindrical assembly without the introduction of astigmatism. Further, the focusing power present in the sagittal plane is due entirely to the four spherical elements plus the two field flatteners, working with the sagittal beam width of 10.8 mm produces an f/15 converging cone at the surface of the greensheet 66.

However, in the tangential plane the optics are different whereby the cylindrical lens doublet closest to the surface of the green sheet 66 has optical power. The tangential height at the polygon facet is now on the order of 0.130 mm reflecting into an f/100 cone. Therefore the six spherical lens elements coupled with the cylindrical doublet constitute a microscope type of assembly operating as a 6.8×reduction system, which has been found to be satisfactory for the sizing of the vias/greensheets in the present invention. This reduces the f/100 cone at the facet to an f/15 tangential cone at the surface of the greensheet 66.

Accordingly, the anamorphic telecentric F-theta scan lens of the present invention, produces both a sagittal and a tangential f/15 spot size of 17 microns at the greensheet plane. This spot size has been found to optimum for the via density/size of the present invention. However, it is to be understood that different spot sizes may be constructed without departing from the spirit and scope of the present invention.

Further, the anamorphic input and output optics also provide the advantage of reducing the pitch angle of the rotating mirror polygon 210, thus providing a more uniform pitch raster from "banding" effects. Additionally, it has been found that the spinner 210 should preferably rotate at a speed of 28,500 rpm in order to provide the proper resolution and speed necessary to scan a greensheet having a high number of vias thereon.

Accordingly, as an overview the optical portion of the present invention collects reflected light from the scanned greensheet in both bright field and darkfield. A fan of fiber optic collectors are arranged symmetrically about a cylindrical lens doublet. There are two trailing fibers, deep trailing and shallow trailing, as well as two leading fibers, deep leading and shallow leading, each representing the two levels of dark field detection. The shallow fiber bundles which consist of 200-1 mm optical fibers are grouped in sub-bundles of 100 each. These shallow fiber bundles see conductive paste fills from flush with the greensheet surface down to at least 40 microns. The deep fibers will measure fills deeper than 80 microns deep. It has been found that the use of two sets of dark field fibers, both trailing and leading assure detection of sloped via fills.

The fifth channel is the bright field channel and works in retro-reflection. Light from the surface of the greensheet or the conductive paste returns toward the hole in the center beam splitter. The beam splitter folds the bright field light through a set of crossed cylinder lenses and into the entrance pupil of a lens. This channel contains a polarizer to suppress laser feedback and eliminate sparkle. The lens focuses the collected light down to a single 1 mm fiber optic size. All the fiber assemblies terminate at the photomultiplier sub-system, as described below, which is external to the optics tower 40.

ELECTRONICS SUBSYSTEM

The electronic processing system for the present invention and effectively contained in the electronics console 48 (FIG. 1) is divisible into five main sections, including:

a. Receiver Box: consisting of a photomultiplier tube (PMT) and preamplifier for the PMT, start of scan (SOS), an extra high gain (EHT) control and laser control and monitor;

b. Analog Rack: Analog controller and Analog processor;

c. Fast Buffer Rack: Fast Buffer controller, Fast Buffer card;

d. Feature Extractor Rack: Master card, Slave card, X-Y card; and e. Parameter Combination rack: microprocessor card, interface card, area, size, spacing violation input FIFO, spacing bit memory.

a. Receiver Box

The Receiver box of the present invention has at its heart the Photomultiplier Tube (PMT) and Preamplifier. These devices convert the optical energy received by the various channels (channels 1-5) into electrical signals. Since the output of the PMT is essentially a current source, it is converted to a voltage related signal before introduced as an input to the analog processor (FIG. 10-described more fully below). It has been found that the characteristics of the PMT and the Preamplifier are critical to faithful and accurate signal conversion. Accordingly, the following PMT and Preamplifier characteristics have been found appropriate for use with the preferred embodiment of the present invention:

PMT- the pmt should operate at frequencies over 200 MHz with a gain of 1 A per lumen; and Preamplifier -preferably the operating bandwidth is approximately 40 MHz with the signal-to-noise ratio greater than 30 dB, corresponding to 3% noise at its output.

b. Analog Rack

Analog Processor

The analog processing electronics and characteristics are shown in block diagram form in FIGS. 9 and 10. Generally, the thresholding of the various signals is at two levels, approximately 30% and approximately 85%. Referring now to FIG. 9 there is shown a typical signal with threshold values. Shown is a video signal with a single defect 116, that is where the signal drops below the 30% threshold as shown. This signal is applied or referenced to reference signal 118. Accordingly, digital output signal 120 shows the location of the single defect 116 as a function of the difference of a reference to the actual sample.

In the preferred embodiment of the present invention there are five analog processors in order to process each of the five video signals (channels 1-5). As previously mentioned the video is compared with a stored reference version of a video signal, with a digital output 120 generated each time the threshold is crossed. In the preferred embodiment of the present invention, each processor has two thresholds, a black level threshold used for channels 1-4, and a grey level for the fifth channel.

Referring now to FIG. 10, the block diagram 122 provides a good overview of analog signal processing. A Video signal is introduced at the video input line 124. This video is passed through a switched filter 126 in order to bandlimit the video to preferably around 100 KHz. The filter 126 is switched at the leading and trailing edges to a smaller time constant in order to allow the signal to rapidly reach the average level. This thereby helps increase the overall "throughput" of the analog circuitry and hence operation of the entire inspection system. The video input signal 124 is also introduced to one input of comparators 146, 148. The output of the filter 126 is introduced to a gated sample hold circuit 128 for introduction to Analog-to-Digital converter 130. The output of the A-D converter 130 is introduced to a bus which interconnects it to Random Access Memory unit 134 and Digital-to-Analog converter 138. Control Logic 132 is used to gate/control the switched filter 126, sample hold switch 128 and A-D converter 130. Control logic 132 also has at its output, a read/write control signal which is used to control reading and writing to Random Access Memory (RAM) control address counter 136, while latch signal from control logic 132 is used to gate the D-A converter 138. RAM 134 is interconnected to receive data from A-D converter 130 and introduce it to D-A converter 138. The address locations of RAM 134 is controlled by address counter 136.

The output of D-A converter is introduced to low pass filter 140 with the output of filter 140 introduced to the input of amplifiers 142,144. These amplifiers 142,144 are for threshold levels of minus 0.30 and minus 0.85 respectively. The output of amplifiers 142, 144 are introduced to the remaining inputs of comparators 146,148 respectively. Accordingly, the analog circuitry 122 produces an 85% threshold digital output 150 and a 30% threshold digital output 152.

Accordingly, in the preferred embodiment of the present invention, the video signal is digitized every 4 micro seconds and stored in the 2 megabyte capacity RAM having a 4 micro second access time. While the green sheet is being inspected, this reference signal is played back through a D-A converter and a variable gain stage to remove imperfections in the pedestal and to give an adjustable threshold which is summed with the incoming video in order to produce a digital signal corresponding to grey and black video signal levels.

Analog Controller

The analog controller card has three functions: The provision of an interface to the transport system, i.e. terminating the 'sheet in' and 'inspect' signals as well as generating the 'sheet hold' signal; An interface to the electronics of the receiver by terminating the 'start of scan' signal and the generating the 'EHT hold' signal; and finally to generate all the common control signals required by the analog processor cards and various system signals as required, all of which may be referred to as "housekeeping" matters.

c. Fast Buffer Rack

Fast Buffer Card

The fast buffer cards store the coordinates of the edges of the channel signals and as such are able to store these signals at an extremely high burst rate. In the preferred embodiment of the present invention, this information is at a 11.53 ns period (86.7 MHz) and 1024 features. However, readout of this information can occur at a much slower rate.

In order to enable both reading and writing to take place simultaneously, two memories are used, one being written to while the other is being read. In the preferred embodiment of the present invention, the fast buffer cards only respond to positive edges. In order to process both rising and falling edges of the features, the fast buffers are arranged in pairs with the normal and inverted differential 'latch rising edge' signals reversed between the pairs.

Further in the preferred embodiment of the present invention, the electronics are implemented in emitter coupled logic (ECL), although it is to be understood that TTL or other types of logic could be utilized without departing from the spirit and scope of the present invention.

Fast Buffer Controller

The fast buffer controller generates all the common control signals required by the above recited fast buffer card. These signals are preferably generated from an 86.7 MHz master clock which is synchronized to start the 'start of scan' signal. Accordingly, this clock frequency gives square pixels when the spinner 210 is rotating at the above recited 28,500 rpm. All signal inputs from the analog controller are received on this card, synchronized to the master clock and combined to generate the master channel data.

d. Feature Extractor Rack

In the preferred embodiment of the present invention, data from the inspected greensheet surface 66 is accumulated on a line-by-line basis. However, the results of this data are required on a per via basis. Accordingly, the data from each via in every line must be linked to data from the same via on adjacent lines. Although conventional image processing systems deal with this type of data on a frame-by-frame basis, they wait for all the data to be collected. Obviously, this approach is not acceptable when inspecting a significant amount of at least 16,000 pixels square. Therefore the data is looked at in a slightly different fashion, thereby having the effect of controllably handling this data. The data required from each via is as follows:
  a. the X and Y bounds of the via;
  b. the area of the via;
  c. the X and Y bounds of the shadow area; and
  d. the area of the shadow.

Accordingly, by only considering the above, the system only has to deal with a much lower pair of coordinates in a single scan time which now effectively, in the preferred embodiment of the present invention requires only up to 800 pairs of coordinates with approximately 400 ns per pair of coordinates.

Master Card

The master card of the present invention processes edge data taken from the fast buffer master card. This card stores the edges in a First-In-First-Out (fifo) memory device and outputs the coordinate of the last edge to all the slave cards. When all five slaves have finished processing, the master card requests the next pair of edges from the master fast buffer and repeats this until no more edges are left in the master fast buffer for the related scan line. The master card then starts a new scan line and requests the first set of edges stored in the fifo on the last scan. If they overlap, they are part of the same feature and are combined. In the event that the edges both occur before the stored pair, they are stored as the start of a new feature or area of interest.

Accordingly, the master card updates the limits for a feature on the current line and then tells the slave processors to get data within those limits and process same. When all the slave processors have finished processing, the master processor then gets more date, decides whether the feature is completed and if so, then controls the output of the coordinates to the next parameter combination rack.

Slave Card

The slave cards are all the same but are configured so as to be either black or white slaves. Channels 1 through 4 are used to process the black area and channel 5 is used for processing the white area. This slave card contains the registers required to store hole size information under the control of the master channel. A 13 bit wide by 1024 deep fifo forms a hole store for the previous line's data. A 16 bit Algorithmitic logic unit (ALU) calculates the difference between (threshold) BLIP high and BLIP low coordinates in order to produce a BLIP length. This is used to produce the hole area. By control of the master card, when the feature is finished, it outputs each area to a parameter combination.

X-Y Card

The X-Y card processes data from the white slave processor. It generates the Xmin, Xmax, Ymin and Ymax coordinates for each feature. This card has a 61 bit wide by 1K deep fifo, used to save the hole coordinates from the previous scan line. In this way a composite picture of a hole is generated. In the event that a new feature is started, the four coordinates are stored and if the feature is continued, the four coordinates are updated and stored.

e. Parameter Combination Rack

The parameter combination rack contains the electronics for the size and area processing and also contains the interface card and processor. The processor sends the thresholds to the area and size processing cards and receives the types and coordinates of defects for display/storage purposed. In the preferred embodiment of the present invention, one card processes the four black and one white area, while five cards are used for processing of the size.

Area

The area card, as mentioned, process the four black and one white area generated by the feature extractor, comparing them with computer set thresholds in order to provide five defect signals which are further processed on the size cards.

The function of the area cards is divided into deep channel black area processing, shallow channel black area processing and the like. The shallow channel black area processing is handled the same as for the deep black processing except that the signals are generated by the "horizontal" pair of optical fiber bundles. One area card is used for processing the white area which compares the number with the computer set threshold and output a defect, called as "substrate-in-hole", in the event a predetermined threshold level is exceeded.

Size

The size card process the X and the Y coordinates of each feature from feature extractors and compares the result with the predetermined set threshold, which in turn may give an oversize defect signal. This card also compares the results with a fixed threshold which defines whether the coordinates are sent for spacing violation processing or whether they are simply too large. All defects such as an underfilled, empty and substrate-in-hole defect will be stored in fifo. This size cards also sends the Xmax, Ymax, Xdiff and Ydiff values to a spacing violation input fifo in order to check for spacing violations.

Spacing Violation Input Fifo

The via limits arrive in the input fifo from the sized card and the computer spacing violation threshold. This fifo is 42 bits wide and 32K bits deep, enabling the spacing violation processing to operate at its own speed without losing any data. Two sets of adders are also used for adding the spacing criterion onto the X and Y coordinates.

Spacing Violation Logic

This logic card contains a system controller which sequences the operations of the various circuits on the logic card. Several of these circuits control the bit memory and are, address counters, read and write signal generators, a clear address counter, a clear write signal generator, a circuit for deciding whether or not the entire bit memory requires clearing and a circuit for selecting logic card also controls the bit memory card and draws the via data into bit memories.

Spacing Violation Bit Memory

This memory is a a bank of memory which may be contained on one or more memory cards. In the preferred embodiment of the present invention, there are two identical cards, bit memory 1 and bit memory 2. Each bit memory bank utilizes 32K×32 bits wide memory. A feature is written a bit at a time under the control of the X/Y addresses from the logic and joint card. This card checks for spacing violations and flags any as well as storing same at the joint fifo.

Interface

This is a general purpose interface between the processing electronics and a data/control bus. This card provides, preferable 8 read and write data strobes each for 16 bit data. A single level interrupt is also implemented. A status register is included at the first read address and a control register at the first write address. Further, fault processing and latching is also contained on the card and is located at the second read address.

Accordingly, the present invention produces apparatus, techniques, methods and the like for the inspection and classification of defects for an area of interest. It is to be remembered that the present invention may be used to inspect a number of items without departing from the spirit and scope of the present invention. Such items may include, for example and not by way of limitation, substrates, semiconductors, surface finishes for not electronic items, fine line details and the like.

Additionally, it is to be understood that may variations of the present invention may be practiced without departing from the spirit and scope of the present invention. For example, the actual layout, types of logic and flow of information with respect may be changed. Additionally, the manner of movement of the item to be inspected may be modified. Further, the number and orientation of the laser light and fiber bundles may be changed.

What is claimed is:

1. An inspection system apparatus, comprising:
   a means for translating in a first direction an item to be inspected;
   at least one optical energy source for generating a light beam;
   means for scanning the light beam across the item to be inspected;

a telecentric lens positioned between the item to be inspected and the scanning means such that the scanned beam maintains a predetermined angle, with respect to an area of interest on the item to be inspected, as it scans thereacross;

a plurality of optic fibers located at a plurality of angles to the item to be inspected, operative so as to receive reflections of the scanned beam from the item to be inspected;

means connected to the optic fibers for converting the reflected light to an electrical signal; and processing means for analyzing the electrical signal, wherein the processing means compares the signal received from a series of scanning lines with reference values.

2. An inspection apparatus as st forth in claim 1 wherein said scanning means includes means for scanning said light beam across the item to be inspected in a direction substantially perpendicular to said first direction.

3. An inspection apparatus as set forth in claim 1 wherein said item to be inspected is translated on an air track.

4. An inspection apparatus as set forth in claim 1 wherein said item to be inspected is an individual circuit board layer adapted to be combined with similar layers into a multilayer ceramic substrate, said layer having a plurality of vias passing there through, and wherein said apparatus operates in a first mode to scan said light beam across a portion of said circuit board layer containing no vias to obtain said reference values and wherein said apparatus operates in a second mode to scan said light beam across the entire region of said layer containing said vias to obtain said electrical signal.

5. An inspection apparatus as set forth in claim 1 wherein said optical energy source is a laser.

* * * * *